(12) United States Patent
Meyer et al.

(10) Patent No.: US 9,149,589 B2
(45) Date of Patent: Oct. 6, 2015

(54) METHOD AND DEVICE FOR PERFORMING ORIENTATION DEPENDENT OSCILLATING POSITIVE EXPIRATORY PRESSURE THERAPY

(75) Inventors: Adam Meyer, London (CA); Noel Gulka, London (CA)

(73) Assignee: Trudell Medical International, London, Ontario (CA)

( * ) Notice: Subject to any disclaimer, the term of this patent is extended or adjusted under 35 U.S.C. 154(b) by 922 days.

(21) Appl. No.: 13/154,103

(22) Filed: Jun. 6, 2011

(65) Prior Publication Data

US 2011/0290240 A1  Dec. 1, 2011

Related U.S. Application Data

(63) Continuation-in-part of application No. 12/711,032, filed on Feb. 23, 2010, now Pat. No. 8,485,179.

(60) Provisional application No. 61/154,661, filed on Feb. 23, 2009, provisional application No. 61/181,200, filed on May 26, 2009.

(51) Int. Cl.
*A61M 16/00* (2006.01)
*A61M 11/06* (2006.01)
(Continued)

(52) U.S. Cl.
CPC ............... *A61M 16/00* (2013.01); *A61M 11/06* (2013.01); *A61M 15/002* (2014.02); *A61M 16/0006* (2014.02); *A63B 23/18* (2013.01);
(Continued)

(58) Field of Classification Search
CPC .............. A61M 11/06; A61M 15/002; A61M 15/0086; A61M 15/009; A61M 16/00; A61M 16/0006; A61M 16/208; A61M 2205/215; A61M 2205/581; A61M 2205/583; C12Q 1/6883; C12Q 2600/136; C12Q 2600/158
USPC ............. 128/200.24, 200.14, 205.19, 205.16, 128/204.18
See application file for complete search history.

(56) References Cited

U.S. PATENT DOCUMENTS

| 393,869 | A | 12/1888 | Warren |
| 938,808 | A | 11/1909 | Yount |

(Continued)

FOREIGN PATENT DOCUMENTS

| EP | 0 372 148 A1 | 6/1990 |
| EP | 0 678 306 A2 | 10/1995 |

(Continued)

OTHER PUBLICATIONS

U.S. Appl. No. 13/674,340, filed Nov. 12, 2012, Grychowski et al.

(Continued)

*Primary Examiner* — Nicholas Lucchesi
*Assistant Examiner* — Weng Lee
(74) *Attorney, Agent, or Firm* — Brinks Gilson & Lione

(57) ABSTRACT

A respiratory device comprising a housing enclosing a chamber and an orientation indicator moveable with respect to the housing between a first position indicative of an orientation of the housing predetermined to be suitable for operation of the respiratory device, and a second position indicative of an orientation of the respiratory device predetermined to be less suitable for operation of the respiratory device. The orientation indicator is positioned in a location on the respiratory device visible to a user during the operation of the respiratory device.

30 Claims, 15 Drawing Sheets

(51) Int. Cl.
  *A61M 15/00*  (2006.01)
  *A63B 23/18*  (2006.01)
  *A61M 16/20*  (2006.01)

(52) U.S. Cl.
  CPC ......... *A61M 15/009* (2013.01); *A61M 15/0086* (2013.01); *A61M 16/208* (2013.01); *A61M 2205/215* (2013.01); *A61M 2205/581* (2013.01); *A61M 2205/583* (2013.01)

(56) References Cited

U.S. PATENT DOCUMENTS

| | | |
|---|---|---|
| 2,670,739 A | 3/1954 | NcNeil |
| 2,918,917 A | 12/1959 | Emerson |
| 3,710,780 A | 1/1973 | Milch |
| 3,908,987 A | 9/1975 | Boehringer |
| 4,054,134 A | 10/1977 | Kritzer |
| 4,062,358 A | 12/1977 | Kritzer |
| 4,182,366 A | 1/1980 | Boehringer |
| 4,198,969 A | 4/1980 | Virag |
| 4,221,381 A | 9/1980 | Ericson |
| 4,226,233 A | 10/1980 | Kritzer |
| 4,231,375 A | 11/1980 | Boehringer et al. |
| 4,267,832 A | 5/1981 | Hakkinen |
| 4,275,722 A | 6/1981 | Sorensen |
| 4,298,023 A | 11/1981 | McGinnis |
| 4,327,740 A | 5/1982 | Shuman |
| 4,403,616 A | 9/1983 | King |
| 4,436,090 A | 3/1984 | Darling |
| 4,470,412 A | 9/1984 | Nowacki et al. |
| 4,601,465 A | 7/1986 | Roy |
| 4,611,591 A | 9/1986 | Inui et al. |
| 4,635,631 A | 1/1987 | Izumi |
| 4,651,731 A | 3/1987 | Vicenzi et al. |
| 4,739,987 A | 4/1988 | Nicholson |
| 4,770,413 A | 9/1988 | Green |
| 4,973,047 A | 11/1990 | Norell |
| 4,981,295 A | 1/1991 | Belman et al. |
| 5,018,517 A | 5/1991 | Liardet |
| 5,042,467 A | 8/1991 | Foley |
| 5,065,746 A | 11/1991 | Steen |
| 5,193,529 A | 3/1993 | Labaere |
| 5,345,930 A | 9/1994 | Cardinal et al. |
| 5,381,789 A | 1/1995 | Marquardt |
| 5,451,190 A | 9/1995 | Liardet |
| 5,479,920 A | 1/1996 | Piper et al. |
| 5,540,220 A | 7/1996 | Gropper et al. |
| 5,569,122 A | 10/1996 | Cegla |
| 5,570,682 A | 11/1996 | Johnson |
| 5,598,839 A | 2/1997 | Niles et al. |
| 5,613,489 A | 3/1997 | Miller |
| 5,645,049 A | 7/1997 | Foley et al. |
| 5,647,345 A | 7/1997 | Saul |
| 5,655,520 A | 8/1997 | Howe |
| 5,658,221 A | 8/1997 | Hougen |
| 5,791,339 A | 8/1998 | Winter |
| 5,829,429 A | 11/1998 | Hughes |
| 5,848,588 A | 12/1998 | Foley et al. |
| 5,862,802 A | 1/1999 | Bird |
| 5,890,998 A | 4/1999 | Hougen |
| 5,893,361 A | 4/1999 | Hughes |
| 5,899,832 A | 5/1999 | Hougen |
| 5,910,071 A | 6/1999 | Hougen |
| 5,925,831 A | 7/1999 | Storsved |
| 6,026,807 A | 2/2000 | Puderbaugh et al. |
| 6,044,841 A | 4/2000 | Verdun et al. |
| 6,058,932 A | 5/2000 | Hughes |
| 6,066,101 A | 5/2000 | Johnson |
| 6,083,141 A | 7/2000 | Hougen |
| 6,089,105 A | 7/2000 | Ricciardelli |
| 6,102,038 A | 8/2000 | DeVries |
| 6,167,881 B1 | 1/2001 | Hughes |
| 6,176,235 B1 | 1/2001 | Benarrouch et al. |
| D440,651 S | 4/2001 | Foran |
| 6,240,917 B1 | 6/2001 | Andrade |
| 6,253,766 B1 | 7/2001 | Niles |
| 6,293,279 B1 | 9/2001 | Schmidt et al. |
| 6,340,025 B1 | 1/2002 | Van Brunt |
| 6,345,617 B1 | 2/2002 | Engelbreth et al. |
| 6,412,481 B1 | 7/2002 | Bienvenu et al. |
| 6,500,095 B1 | 12/2002 | Hougen |
| 6,557,549 B2 | 5/2003 | Schmidt et al. |
| 6,581,595 B1 | 6/2003 | Murdock et al. |
| 6,581,596 B1 | 6/2003 | Truitt |
| 6,581,598 B1 | 6/2003 | Foran et al. |
| 6,581,600 B2 | 6/2003 | Bird |
| 6,595,203 B1 | 7/2003 | Bird |
| 6,606,989 B1 | 8/2003 | Brand |
| 6,615,831 B1 | 9/2003 | Tuitt |
| 6,631,721 B1 | 10/2003 | Salter et al. |
| 6,659,100 B2 | 12/2003 | O'Rourke |
| 6,702,769 B1 | 3/2004 | Fowler-Hawkins |
| 6,708,690 B1 | 3/2004 | Hete et al. |
| 6,708,691 B1 | 3/2004 | Hayek |
| 6,726,598 B1 | 4/2004 | Jarvis |
| D490,519 S | 5/2004 | Pelerossi et al. |
| 6,776,159 B2 | 8/2004 | Pelerossi et al. |
| 6,848,443 B2 | 2/2005 | Schmidt et al. |
| 6,851,425 B2 | 2/2005 | Jaffre |
| 6,904,906 B2 | 6/2005 | Salter |
| 6,923,181 B2 | 8/2005 | Tuck |
| 6,929,007 B2 | 8/2005 | Emerson |
| 6,984,214 B2 | 1/2006 | Fowler-Hawkins |
| 7,059,324 B2 | 6/2006 | Pelerossi et al. |
| 7,096,866 B2 | 8/2006 | Be'eri et al. |
| 7,134,434 B2 | 11/2006 | Truitt et al. |
| 7,165,547 B2 | 1/2007 | Truitt et al. |
| 7,188,621 B2 | 3/2007 | DeVries |
| 7,191,776 B2 | 3/2007 | Niles |
| 7,191,780 B2 | 3/2007 | Faram |
| 7,214,170 B2 | 5/2007 | Sumners et al. |
| 7,699,054 B2 | 4/2010 | Pelerossi et al. |
| 7,717,847 B2 | 5/2010 | Smith |
| 7,771,472 B2 | 8/2010 | Hendricksen et al. |
| 7,798,148 B2 | 9/2010 | Doshi et al. |
| 7,856,979 B2 | 12/2010 | Doshi |
| 8,006,922 B2 | 8/2011 | Katzer |
| 8,025,051 B2 | 9/2011 | Dagsland |
| 8,118,024 B2 | 2/2012 | DeVries et al. |
| 2005/0181918 A1 | 8/2005 | Sumners et al. |
| 2006/0090753 A1 | 5/2006 | Pelerossi et al. |
| 2007/0113843 A1 | 5/2007 | Hughes |
| 2007/0256690 A1 | 11/2007 | Faram |
| 2007/0259759 A1 | 11/2007 | Sumners et al. |
| 2008/0000477 A1 | 1/2008 | Huster et al. |
| 2008/0053456 A1 | 3/2008 | Brown et al. |
| 2008/0066754 A1 | 3/2008 | Faram |
| 2008/0078383 A1 | 4/2008 | Richards et al. |
| 2008/0110451 A1 | 5/2008 | Dunsmore et al. |
| 2008/0110455 A1 | 5/2008 | Dunsmore et al. |
| 2008/0228113 A1 | 9/2008 | Meyer et al. |
| 2010/0101573 A1 | 4/2010 | Meyer et al. |
| 2010/0139655 A1 | 6/2010 | Genosar |
| 2011/0290240 A1 | 12/2011 | Meyer et al. |
| 2012/0097164 A1 | 4/2012 | Rozario et al. |

FOREIGN PATENT DOCUMENTS

| | | |
|---|---|---|
| EP | 1 435 251 | 12/2003 |
| EP | 1 464 357 A1 | 10/2004 |
| EP | 1 435 251 B1 | 6/2006 |
| EP | 1 103 287 B1 | 6/2007 |
| EP | 1 897 576 | 8/2007 |
| EP | 1 897 576 A1 | 3/2008 |
| EP | 1 908 489 A1 | 4/2008 |
| EP | 2444114 | 4/2012 |
| EP | 2455137 | 5/2012 |
| GB | 2 425 488 A | 11/2006 |
| WO | WO 89/03707 A1 | 5/1989 |
| WO | WO 96/40376 | 12/1996 |
| WO | WO 99/16490 | 4/1999 |
| WO | WO 00/27455 | 5/2000 |
| WO | WO 2007/061648 A3 | 5/2007 |
| WO | WO 2007/119104 A3 | 10/2007 |

(56) References Cited

FOREIGN PATENT DOCUMENTS

| WO | WO 2008/063966 A1 | 5/2008 |
| WO | WO 2008/122045 A1 | 10/2008 |
| WO | WO2009/131964 | 10/2009 |
| WO | WO2011/058470 | 5/2011 |
| WO | WO 2012/038864 A2 | 3/2012 |

OTHER PUBLICATIONS

U.S. Appl. No. 29/438,878, filed Dec. 4, 2012, Meyer.
U.S. Appl. No. 12/711,032, filed Feb. 23, 2010, Meyer et al.
U.S. Appl. No. 12/472,215, filed May 26, 2009, Meyer et al.
Web page entitled Bronchial Hygiene, acapella Vibratory PEP Therapy System accessed from http://www.smiths-medical.com/catalog/bronchial-hygiene/acapella/acapella.html on Jul. 7, 2009.
Web page entitled Thayer Quake accessed from http://www.thayermedical.com/quake.htm on Jul. 7, 2009.
U.S. Appl. No. 11/845,898, filed Mar. 6, 2008, Brown et al.
U.S. Appl. No. 12/857,925, filed Dec. 9, 2010, Dunsmore et al.
Human growth hormone, cortisol, and acid-base balance changes after hyperventilation and breath-holding; PubMed—indexed for Medline; Int J Sports Med., Dec. 1986; 7(6):311-5, Djarova T., Iikov A., Varbanova A., Nikiforova A., Mateev G.
Bosco C, Cardinale M. & Tsarpela O (1999). Influence of vibration on mechanical power and electromyogram activity in human arm flexor muscles. Eur J Appl Physiol 79, 306-311.
Breathtaking News; Aug. 10, 2007.
U.S. Appl. No. 13/489,894, filed Jun. 6, 2012, Meyer et al.
PCT International Search Report for PCT/IB2012/001089, Oct. 5, 2012.
PCT International Written Opinion for PCT/IB2012/001089, Oct. 5, 2012.
David Sumners; Power Breathing and Strength; http://EzineArticles.com/972576 Published Feb. 11, 2008.
Good Vibrations blog; http://vibrotraining.blogspot.com, Earliest posting Jan. 17, 2008.

METHOD AND DEVICE FOR PERFORMING ORIENTATION DEPENDENT OSCILLATING POSITIVE EXPIRATORY PRESSURE THERAPY

RELATED APPLICATIONS

This is a continuation-in-part of U.S. application Ser. No. 12/711,032, filed on Feb. 23, 2010, now U.S. Pat. No. 8,485,179, which claims the benefit of U.S. Provisional Application No. 61/154,661, filed on Feb. 23, 2009, and U.S. Provisional Application No. 61/181,200, filed on May 26, 2009, all of which are incorporated herein by reference.

TECHNICAL FIELD

The present disclosure relates to a respiratory treatment device, and in particular, to an orientation dependent oscillating positive expiratory pressure ("OPEP") device.

BACKGROUND

Each day, humans may produce upwards of 30 milliliters of sputum, which is a type of bronchial secretion. Normally, an effective cough is sufficient to loosen secretions and clear them from the body's airways. However, for individuals suffering from more significant bronchial obstructions, such as collapsed airways, a single cough may be insufficient to clear the obstructions.

OPEP therapy represents an effective bronchial hygiene technique for the removal of bronchial secretions in the human body and is an important aspect in the treatment and continuing care of patients with bronchial obstructions, such as those suffering from chronic obstructive lung disease. It is believed that OPEP therapy, or the oscillation of exhalation pressure at the mouth during exhalation, effectively transmits an oscillating back pressure to the lungs, thereby splitting open obstructed airways and loosening the secretions contributing to bronchial obstructions.

OPEP therapy is an attractive form of treatment because it can be easily taught to most hospitalized patients, and such patients can assume responsibility for the administration of OPEP therapy throughout their hospitalization and also once they have returned home. To that end, a number of portable OPEP devices have been developed.

BRIEF SUMMARY

In one aspect, a respiratory device includes a housing enclosing a chamber and an orientation indicator moveable with respect to the housing between a first position indicative of an orientation of the housing predetermined to be suitable for the operation of the respiratory device, and a second position indicative of an orientation of the housing predetermined to be less suitable for operation of the respiratory device. The orientation indicator may be positioned in a location on the respiratory device visible to a user during the operation of the respiratory device.

In another aspect, the respiratory device may be an OPEP device. Alternatively, the respiratory device may be a nebulizer.

In another aspect, an OPEP device includes a housing enclosing a chamber, a chamber inlet, a chamber outlet, and a channel positioned in an exhalation flow path between the chamber inlet and the chamber outlet. An air flow regulator is moveable with respect to the channel. Furthermore, an orientation indicator is moveable with respect to the housing between a first position indicative of an orientation of the housing predetermined to be suitable for administration of OPEP therapy to a user, and a second position indicative of an orientation of the housing predetermined to be less suitable for administration of OPEP therapy to the user. The orientation indicator may be positioned in a location on the OPEP device visible to the user during the administration of OPEP therapy.

In another aspect, the orientation indicator moves in response to a change in the orientation of the housing. A weight of the orientation indicator may bias the orientation indicator in the direction of gravity. As such, the orientation indicator may be moveable in at least one direction.

In another aspect, the respiratory device or the OPEP device may include a capsule enclosing the orientation indicator. The capsule may include an indicia for identifying a portion of the capsule in which the presence of the orientation indicator indicates an orientation of the housing predetermined to be suitable for the operation of the respiratory device, or for the administration of OPEP therapy. The capsule may be shaped so that the orientation indicator moves to the first position in response to a change in the orientation of the housing to an orientation predetermined to be suitable for operation of the respiratory device, or for the administration of OPEP therapy.

In yet another aspect, the orientation indicator may be a sphere. The orientation indicator may also be a fluid. Alternatively, the orientation indicator may be in the form of a meter needle.

In another aspect, the chamber inlet may be configured to receive exhaled air into the chamber, while the chamber outlet may be configured to permit exhaled air to exit the chamber.

In a further aspect, a respiratory device includes a housing enclosing a chamber and an orientation indicator configured to provide visual or auditory feedback to a user indicative of the suitability of the orientation of housing predetermined to be suitable for the administration of the respiratory therapy.

In another aspect, the orientation indicator includes a micro electro-mechanical system gyroscope configured to sense the orientation of the housing. The orientation indicator may also include at least one light for indicating the suitability of the orientation of the housing for the administration of OPEP therapy. The orientation may also include an audio signaling device for indicating the suitability of the orientation of the housing for the administration of OPEP therapy.

In yet another aspect, a method of administering orientation dependent OPEP therapy includes passing a flow of exhaled air along an exhalation flow path defined between an inlet and an outlet of a chamber in an OPEP device, maintaining an air flow regulator in a channel positioned in the exhalation flow path for restricting the flow of exhaled air through the channel, and moving the air flow regulator in repose to the flow of exhaled air repeatedly between a first position where the flow of exhaled air is restricted and a second position where the flow of exhaled air is less restricted. The method also involves the step of orienting the OPEP device based on feedback provided by an orientation indicator on the OPEP device. The orientation indicator may provide either visual feedback or auditory feedback to indicate the suitability of the orientation of the OPEP device for the administration of OPEP therapy.

In a further aspect, a method of administering nebulizer therapy includes providing a liquid stored in a reservoir, providing a source of pressurized gas, and aerosolizing the liquid with the pressurized gas. The method further includes orienting the nebulizer based on feedback provided by an orientation indicator provided on the nebulizer. The orientation indicator may provide either visual feedback or auditory feedback to indicate the suitability of the orientation of the reservoir for the administration of nebulizer therapy.

BRIEF DESCRIPTION OF THE DRAWINGS

FIG. 1 is a perspective view of an OPEP device;

FIG. 2 is a cross-sectional view of the OPEP device of FIG. 1;

FIG. 3 is a cross-sectional view of a channel assembly of the OPEP device of FIG. 1;

FIG. 4 is a perspective view of an adjustment band of the OPEP device of FIG. 1;

FIGS. 5A-C are cross-sectional views of the OPEP device of FIG. 1, illustrating movement of the adjustment band of FIG. 4 relative to the channel assembly of FIG. 3;

FIG. 6 is a perspective view of the OPEP device of FIG. 1 configured with a nebulizer port for the simultaneous administration of OPEP and aerosol therapies;

FIG. 7 is a side view of an orientation indicator positioned on a portion of the OPEP device of FIG. 1;

FIGS. 8A-C are side views of the orientation indicator of FIG. 7, illustrating the visual feedback of the orientation indicator for various orientations of the OPEP device of FIG. 1;

FIGS. 9A-B are side views of an alternative embodiment of an orientation indicator in the form of a liquid or gas enclosed within a capsule;

FIG. 10 is a side view of an alternative embodiment of an orientation indicator in the form of a meter needle rotatably mounted to a housing;

FIGS. 11A-B are side views of the orientation indicator and the housing of FIG. 10 enclosed by a cover to provide an indicia of orientations of the device associated with the orientation indicator that are suitable and/or ideal for the device's operation;

FIGS. 12A-C are representative views of an alternative embodiment of an orientation indicator in the form of an electrical visual and/or auditory system;

FIG. 13 is a perspective view of a first commercially available OPEP device shown with orientation indicator of FIG. 7;

FIG. 14 is a perspective view of the first commercially available OPEP device shown with the orientation indicator of FIGS. 12A-12C;

FIG. 15 is a perspective view of a second commercially available OPEP device shown with the orientation indicator of FIG. 7;

FIG. 16 is a perspective view of the second commercially available OPEP device shown with the orientation indicator of FIGS. 12A-12C;

FIG. 17 is a perspective view of a commercially available nebulizer shown with the orientation indicator of FIG. 7; and, FIG. 18 is a perspective view of the same commercially available nebulizer shown with the orientation indicator of FIGS. 12A-12C.

DETAILED DESCRIPTION

OPEP therapy is very effective within a range of operating conditions. For example, an adult human may have an exhalation flow rate ranging from 10 to 60 liters per minute, and may maintain a static exhalation pressure in the range of 10 to 20 cm $H_2O$. Within these parameters, OPEP therapy is believed to be most effective when changes in the exhalation pressure range from 5 to 20 cm $H_2O$ oscillating at a frequency of 10 to 40 Hz. In contrast, an adolescent may have a much lower exhalation flow rate, and may maintain a lower static exhalation pressure, thereby altering the operating conditions most effective for OPEP therapy. Likewise, the ideal operating conditions for an athlete may differ from those of an adult. As described below, the disclosed OPEP device is configurable and provides feedback to the user so that ideal operating conditions may be selected and maintained.

Referring first to FIGS. 1-2, an OPEP device 100 is shown. In general, the OPEP device 100 includes a housing 102 enclosing a chamber 114, a chamber inlet 104, and a chamber outlet 106. The housing 102 may also be associated with a mouthpiece 108. Although the mouthpiece 108 is shown as being fixedly attached to the housing 102, it is envisioned that the mouthpiece 108 may be removable and replaceable with a mouthpiece 108 of a different size or shape. Alternatively, other user interfaces, such as breathing tubes or gas masks (not shown) may be associated with the housing 102. Preferably, the housing 102 is openable so that the chamber 114 and the parts contained within the housing 102 can be periodically accessed, cleaned, replaced, or selectively adjusted. The housing 102 may be constructed of any durable material, such as a polymer (e.g., Acrylonitrile Butadiene Styrene).

As shown, the housing 102 is generally egg-shaped. However, a housing of any shape could be used. Furthermore, the chamber inlet 104 and the chamber outlet 106 could be any shape or series of shapes, such as a plurality of circular passages or linear slots. Likewise, the chamber inlet 104 and the chamber outlet 106 may be located elsewhere on the housing 102. More importantly, it should be appreciated that the cross-sectional area of the chamber inlet 104 is but one of the factors influencing the ideal operating conditions described above.

Referring to FIG. 2, a cross-sectional view of the OPEP device 100 shows the components housed in the OPEP device 100. Those components include a channel assembly 116, an adjustment band 163, and inner and outer bushings 162, 164, which may operate to seal the chamber 114 and permit the channel assembly 116 to move relative to the housing 102. The OPEP device 100 also includes an air flow regulator 120 that rests in a channel 118 in the channel assembly 116. The air flow regulator 120 is moveably positioned within the channel 118 such that it is free to move about within the confines of at least a portion of the channel 118.

An exhalation flow path, identified by dotted line 111, is defined between the chamber inlet 104 and the chamber outlet 106. The OPEP device 100 also includes an orientation indicator 158 to provide a user with visual feedback of the orientations of the OPEP device 100 suitable and/or ideal for providing OPEP therapy, as explained in greater detail below. In addition, a transparent window 160 may be included with the housing 102 to permit the user to view the components contained therein, such as those that may be selectively adjusted and/or replaced to obtain the desired operating conditions.

As shown in FIG. 2, the spherical shape of the air flow regulator 120 is adapted to restrict the flow of air through the channel 118. However, other sizes or shapes, such as a conical air flow regulator, could be substituted to achieve a different range of restriction. In general, the air flow regulators shown and described herein are spherical and have a diameter of five-eighths or eleven-sixteenths of an inch. Likewise, the weight of the air flow regulator 120 could be altered by changing the material of the air flow regulator 120. For instance, the air flow regulator 120 could be made from a plastic, aluminum, copper, brass, or steel. In this way, the OPEP device 100 is highly configurable and can be altered according to the prescribed OPEP therapy.

Figure 2:
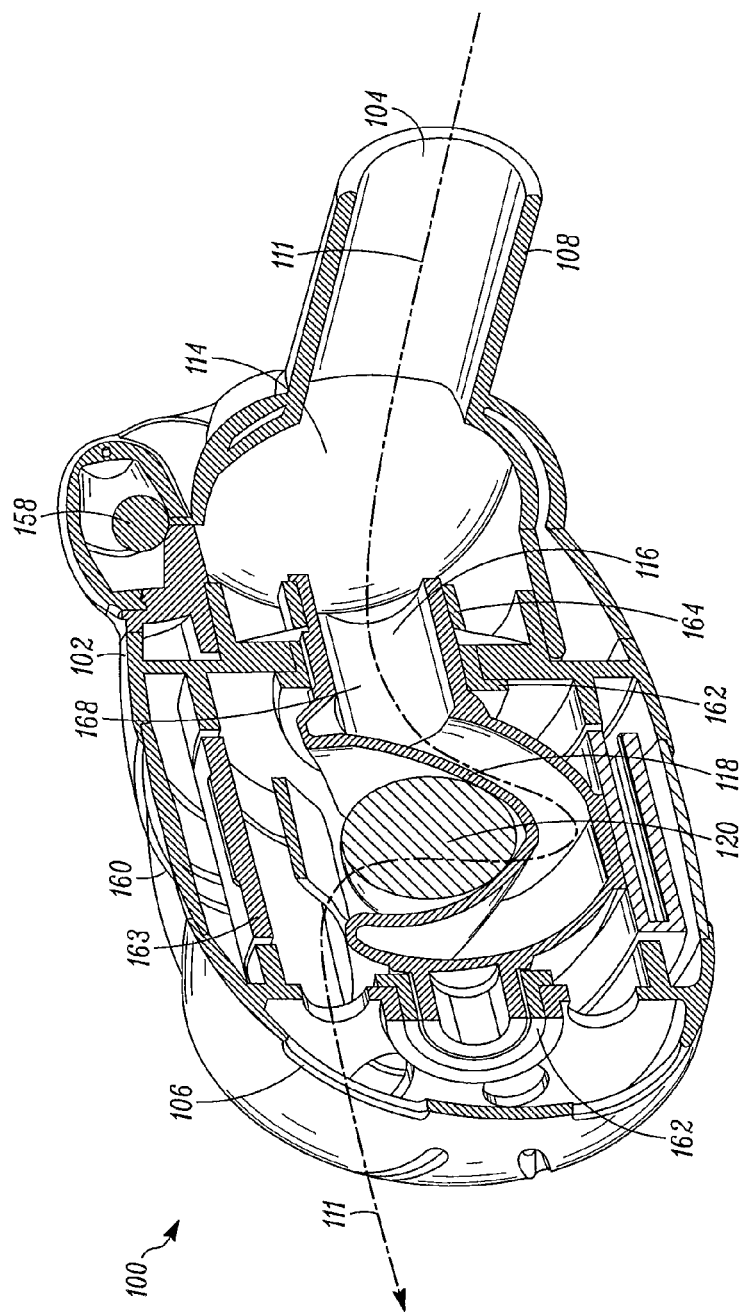
Figure 3:
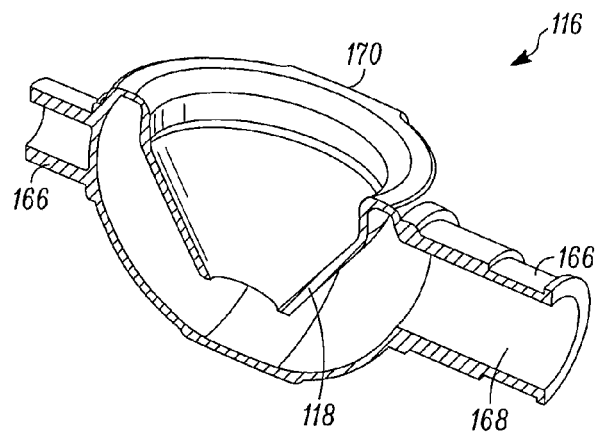

Referring to FIG. 3, a cross-sectional view of the channel assembly 116 is shown. In addition to the channel 118, the channel assembly 116 comprises a pair of cylindrical support surfaces 166 about which the channel assembly 116 may be supported by the inner and outer bushings 162, 164 and pivotably attached to the housing 102 (FIG. 2). In this way, the cylindrical support surfaces 166 act as a gimbal, permitting the channel assembly 116 to rotate relative the housing 102 about an axis defined between the cylindrical support surfaces 166. Furthermore, one of the cylindrical support surfaces 166 forms a passage 168 defining a portion of the exhalation flow path 111, as shown in FIG. 2.

Those skilled in the art will appreciate that the shape of the channel 118 could be altered to achieve a different range of restriction. For example, a portion of the channel 118 in FIG. 3 is shown as being conical, or having the shape of a truncated cone; however, one or more portions of the channel 118 could alternatively, or in combination, be spherical or cylindrical. In view of these variables, it should be appreciated that an important factor affecting the administration of OPEP therapy is the extent to which the air flow regulator 120 restricts the flow of air through the channel 118. Finally, the channel assembly 116 may include an annular surface 170 about which the adjustment band 163 may be mounted.

Figure 4:
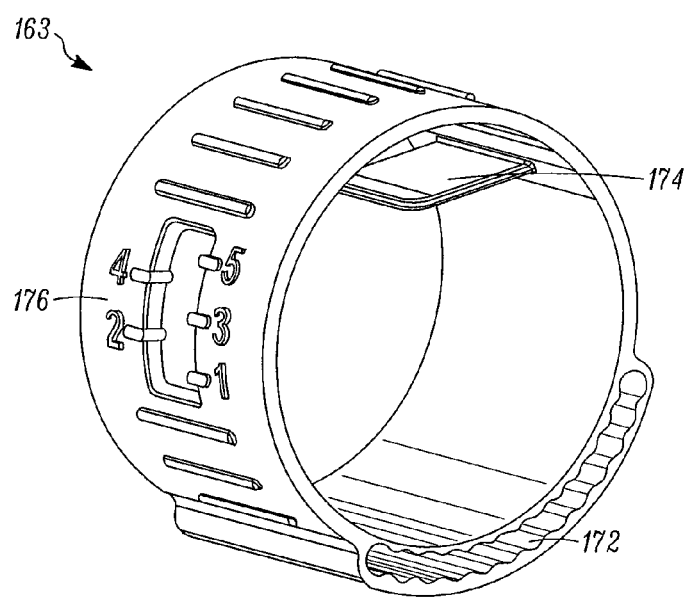

Turning to FIG. 4, the adjustment band 163 of the OPEP device 100 is shown. In general, the adjustment band 163 is shaped and sized to fit around the annular surface 170 (FIG. 3) of the channel assembly 116 such that the adjustment band 163 and the channel assembly 116 are frictionally engaged with one another, but may be rotated relative to one another under minimal force applied by the user. The adjustment band 163 also includes a secondary weight 172, a retaining member 174 to keep the air flow regulator 120 within the channel 118, and a gauge 176 to show the position of the channel assembly 116 relative to the adjustment band 163. Notably, when the adjustment band 163 is mounted to the channel assembly 116, the position of the secondary weight creates a center of mass offset from the axis formed between the cylindrical support surfaces 166, about which the channel assembly 116 is rotatable.

In operation, the OPEP device 100 administers OPEP therapy to a user while he or she exhales into the chamber inlet 104 through the mouthpiece 108. When the OPEP device 100 is positioned in an upright orientation, as shown in FIG. 2, the air flow regulator 120 moves under the force of gravity into a first position, or a resting position, within the channel 118. With the air flow regulator 120 in the first position, the flow of air through the channel 118 is restricted. Depending on the shape and size of the air flow regulator 120 and/or the channel 118, the air flow regulator 120 may restrict some or all of the exhaled air flowing through the channel 118. As the user continues to exhale, the pressure within the chamber 114 increases. As the pressure increases, the force acting on the portion of the air flow regulator 120 restricting the flow of exhaled air through the channel 118 also increases. The force acting on the air flow regulator 120 continues to increase during exhalation until the force of gravity acting on the air flow regulator 120 is overcome, and the air flow regulator 120 moves from the first position to a second position in the channel 118.

In the second position, the air flow regulator 120 is lifted away from the resting position near the bottom of the channel 118. Depending on the shape and size of the air flow regulator 120 and/or the channel 118, the air flow regulator 120 may roll, slide, or jump to the second position. With the air flow regulator 120 in the second position, the flow of air through the channel 118 is less restricted than the flow of air through the channel 118 when the air flow regulator 120 is in the first position. As such, more air is permitted to traverse the channel 118 and exit the chamber outlet 106. In this way, the weight of the air flow regulator 120 offers a resistance to the flow of exhaled air through the channel 118 during exhalation.

After the airflow regulator 120 moves to the second position, and the flow of air through the channel 118 increases, the pressure in the chamber 114 begins to drop. As the pressure decreases, the force acting on the portion of the air flow regulator 120 restricting the flow of air through the channel 118 also decreases. When this force drops below the force of gravity acting on the air flow regulator 120, the air flow regulator 120 returns to the first position, thereby increasing the restriction on the flow of air through the channel 118, and causing the pressure in the chamber 114 to rise again. As a user continues to exhale, this process repeats itself, effectively generating an oscillating pressure in the chamber 114. This oscillating pressure is in turn transmitted back through the chamber inlet 104 and into the respiratory system of the user, providing him or her with OPEP therapy.

As previously explained, the weight of the air flow regulator 120 offers a resistance to the flow of air through the channel 118. While the air flow regulator 120 is in the first position, the force of gravity acting on the air flow regulator 120 is balanced by the force derived from the exhalation pressure in the chamber 114 and the normal force from the channel 118 acting on the air flow regulator 120. Accordingly, if the orientation of the channel 118 were to change, the magnitude and direction of the normal force from the channel 118 would change, as would the direction of the force acting on the air flow regulator 120 derived from the exhalation pressure in the chamber 114. The direction and magnitude of gravitational forces acting on the air flow regulator 120, however, would remain unchanged. Put another way, a change in the orientation of the OPEP device 100 may increase or decrease the incline of the channel 118 the air flow regulator 120 must traverse to arrive at the second position. Thus, the orientation of the channel 118, along with the position of the air flow regulator 120 within the channel 118, could prevent the air flow regulator 120 from sufficiently restricting the flow of air through the channel 118, such that the administration of OPEP therapy would not be suitable and/or ideal, or alternatively, altogether impossible.

One advantage of the OPEP device 100 is its ability to reduce the effect of the orientation of the OPEP device 100 on the effective administration of OPEP therapy. More specifically, as the housing 102 is rotated about the axis defined between the cylindrical support surfaces 166, gravity acting on the secondary weight 172 in the adjustment band 163 causes the channel assembly 116, and thus the channel 118, to rotate relative to the housing 102 to a position where the secondary weight 172 is below the axis between the cylindrical support surfaces 166. To aid in the creation of a seal, yet maintain mobility of the channel assembly 116, the support surfaces 166 and the inner and outer bushings 162, 164 may be made of suitable low friction materials (e.g., acetyl, nylon, etc.). Alternatively, a lubricant could be applied to the supporting surfaces 166 and the inner and outer bushings 162, 164. In this way, the orientation of the channel assembly 116 does not substantially change as the orientation of the housing 102 is rotated about the axis defined between the cylindrical support surfaces 166. To the extent the orientation of the housing 102 is rotated about the axis perpendicular to the axis defined between the cylindrical support surfaces 166, the orientation indicator 158 provides the user with visual feedback of suitable and/or ideal orientations for the administration of OPEP therapy, as explained below.

The OPEP device 100 is also selectively adjustable to obtain the desired operating conditions of the OPEP therapy. As previously explained, the oscillation frequency and the amplitude of the OPEP therapy is dependent upon, amongst other variables, the angle of the channel 118 that contacts the air flow regulator 120, the normal force supplied by the channel 118 against the air flow regulator 120, and the direction of gravity relative thereto.

Figure 5C:
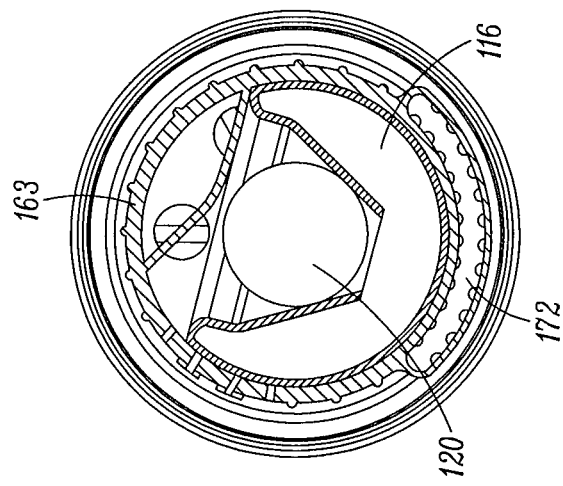
Figure 5B:
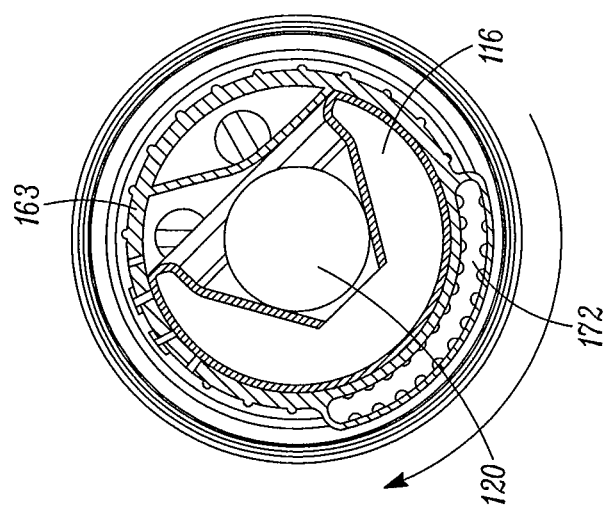
Figure 5A:
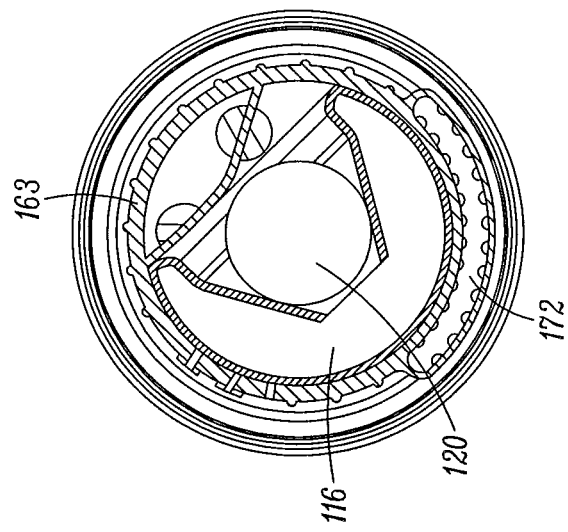

As shown in FIG. 2, the adjustment band 163 and the channel assembly 116 may be frictionally engaged with one another about the annular surface 170 of the channel assembly 116 such that both the channel assembly 116 and the adjustment band 163 are supported by the inner and outer bushings 162, 164 and pivotably attached to the housing 102. Referring to FIGS. 5A-C, an illustration is provided showing the selective rotation of the adjustment band 163 relative to the channel assembly 116. A user may accomplish such an adjustment by opening the housing 102 to access the components contained therein, or by any other suitable means.

In FIG. 5A, the channel assembly 116 is shown in one possible orientation relative to the adjustment band 163. Notably, the secondary weight 172 is located below the axis defined between the support surfaces 166 (see FIG. 2), as the force of gravity biases the adjustment band 163 and secondary weight 172 to this location. To adjust the frequency and amplitude of the OPEP therapy provided by the OPEP device 100, a user may overcome the frictional engagement between the adjustment band 163 and the channel assembly 116 to rotate the adjustment band 163 relative to the channel assembly 116, as shown in FIG. 5B. Then, as shown in FIG. 5C, once the adjustment band 163 is released and the frictional engagement re-established, the adjustment band 163, and thus the channel assembly 116, will rotate under the force of gravity back to a position where the secondary weight 172 is located under the axis defined between the cylindrical support surfaces 166. By adjusting the orientation of the channel assembly 116 relative to the adjustment band 163 shown in FIG. 5A to the orientation shown in FIG. 39C, the angle of the channel 118 that contacts the air flow regulator 120, the normal force supplied by the channel 118, and the direction of gravity relative thereto will also have changed. As shown in FIG. 2, such orientations may be viewed by the user through the transparent window 160 included with the housing 102. Furthermore, predetermined orientations may be selected by the user according to the gauge 176 located on the adjustment band 163.

Figure 6:
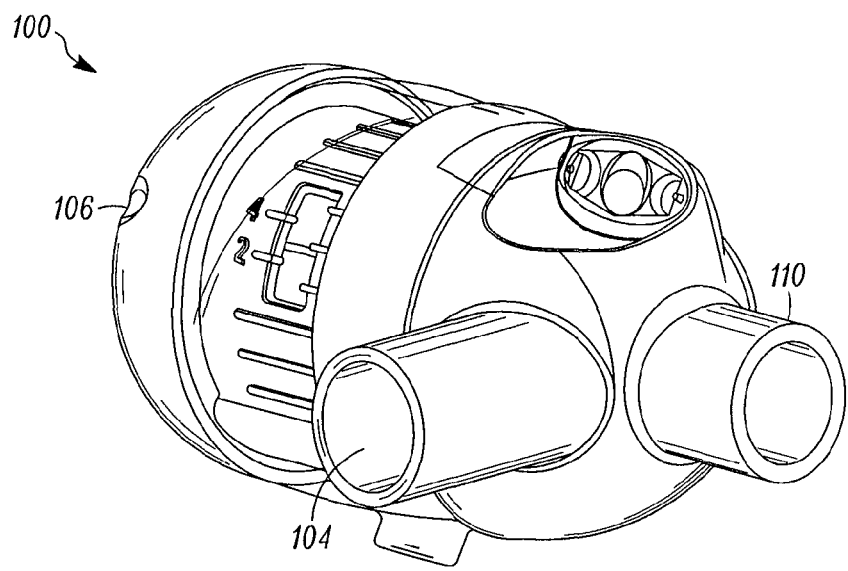

Referring now to FIG. 6, the OPEP device 100 may also be adapted to provide simultaneous administration of OPEP and nebulizer therapies. As shown, the OPEP device 100 may include a nebulizer port 110 connectable to any number of commercially available nebulizers, such as the AERO-ECLIPSE® II breath-actuated nebulizer available from Trudell Medical International of London, Canada. Descriptions of suitable nebulizers may be found in U.S. Pat. Nos. 4,150,071; 5,287,847; 5,584,285; 5,823,179; 6,085,741, the entireties of which are herein incorporated by reference.

The nebulizer port 110 may also include a one-way valve (not shown) configured to open on inhalation and close on exhalation. In this configuration, an inhalation flow path is formed between the nebulizer port 110 and the chamber inlet 104 via the chamber 114. If the OPEP device 100 is connected to a nebulizer, an aerosol medicament may be drawn from the nebulizer into the respiratory system of the user upon inhalation. If the OPEP device 100 is not connected to a nebulizer, the user may inhale through the nebulizer port 110 the air surrounding the OPEP device 100, or air from a stand-alone air supply connected to the nebulizer port 110. However, in both cases, exhaled air is forced to traverse the channel 118 and exit the OPEP device 100 through the chamber outlet 106. Alternatively, the OPEP device 100 may include a separate inhalation valve (not shown) or omit the nebulizer port 110 altogether, in which case the user would have to inhale through a source external to the OPEP device 100, such as through his or her nose. Notably, the inhalation flow path from the nebulizer port 110 to the mouthpiece 108 bypasses the channel 118, thereby reducing the potential for loss of expensive medicament.

Figure 1:
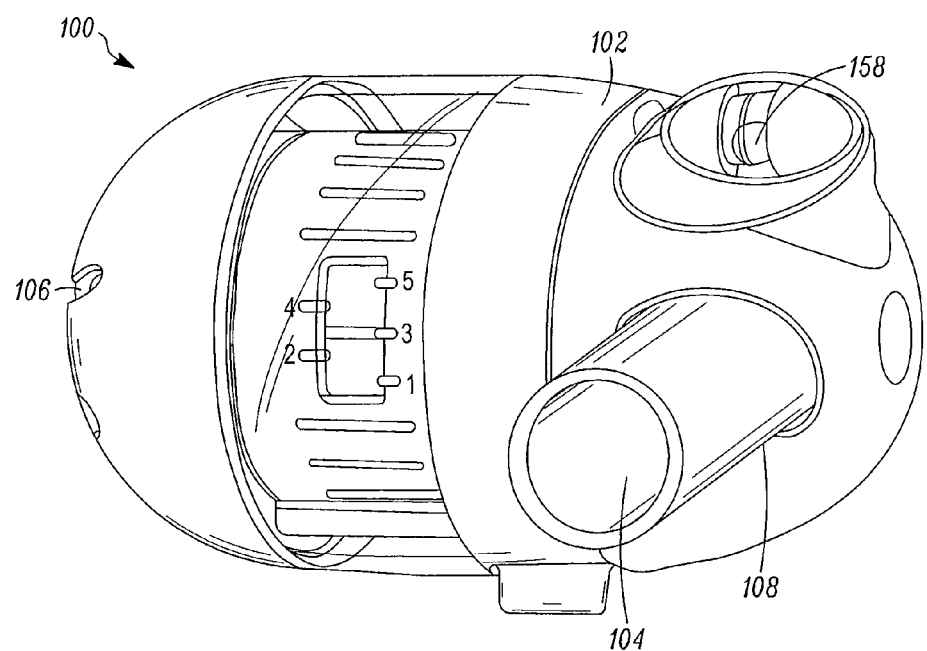
Figure 7:
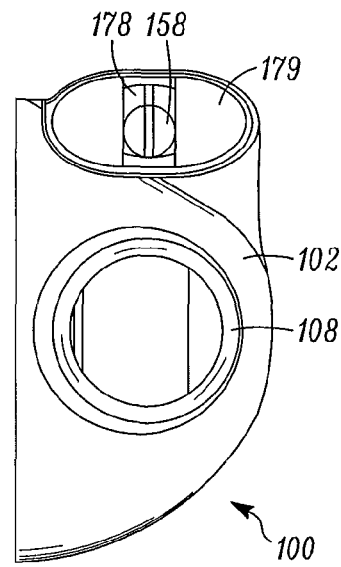

As illustrated in FIGS. 1-2 and described above, the OPEP device 100 may include an orientation indicator 158 to provide a user with visual feedback of the suitable and/or ideal orientation of the OPEP device 100 for the administration of OPEP therapy. By way of example, FIG. 7 shows a portion of the OPEP device 100 with an orientation indicator 158 positioned on the housing 102 in a location relative to the mouthpiece 108 such that, as the user exhales into the mouthpiece 108, the user is able to view the orientation indicator 158 to determine whether the orientation of the OPEP device 100 is suitable and/or ideal for the administration of OPEP therapy. In this regard, a user is able to adjust the orientation of the OPEP device 100 in response to the visual feedback received from the orientation indicator 158 during the administration of OPEP therapy.

As shown in FIGS. 2 and 7, the orientation indicator 158 is enclosed by a capsule 178. The indicator 158 may be comprised of any suitable material, such as a plastic, and may be spherically shaped. The capsule 178 may be shaped like a pair of cones whose bases are coplanar, such that the angles of the conic sections define the range of orientations suitable and/or ideal for the administration of OPEP therapy (e.g., +/−10°). However, the capsule 178 could comprise any number of other shapes depending on the range of desired orientations.

The capsule 178 may be connected to the OPEP device 100 such that movement of the OPEP device 100 within the predetermined range of orientations causes the indicator 158 to remain in a portion of the capsule 178 near the coplanar bases, thus indicating a suitable and/or ideal orientation of the OPEP device 100 for the administration of OPEP therapy. Likewise, the capsule 178 may be shaped and connected to the OPEP device 100 such that movement of the OPEP device 100 within a separate predetermined range of orientations causes the indicator 158 to move to a portion of the capsule 178 near either tip of one of the pair of cones, thereby indicating an orientation of the OPEP device 100 not suitable or ideal for the administration of OPEP therapy. As a further aid to the user, the capsule 178 may include an indicia identifying the portion of the capsule 178 in which the presence of the indicator 158 indicates an orientation of the OPEP device 100 suitable and/or ideal for the administration of OPEP therapy. In FIG. 7, for example, the indicia is a non-transparent material or coating 179 surrounding the capsule 178.

Figure 8C:
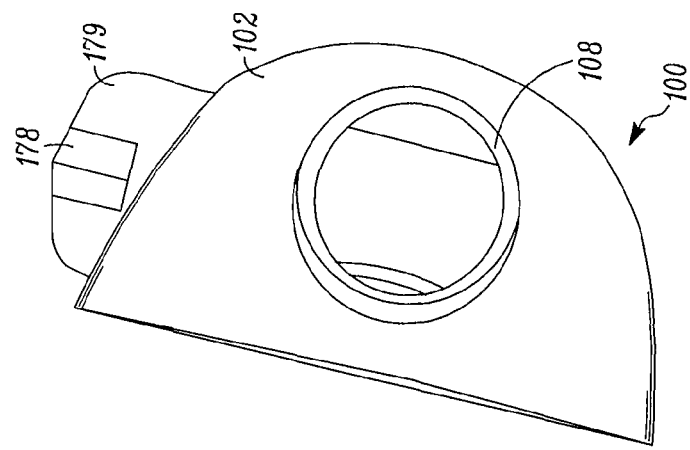
Figure 8B:
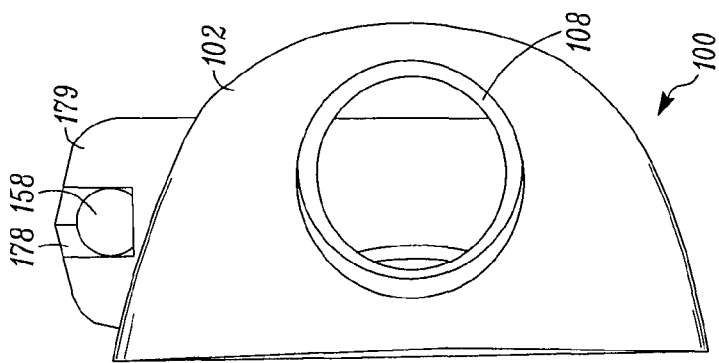
Figure 8A:
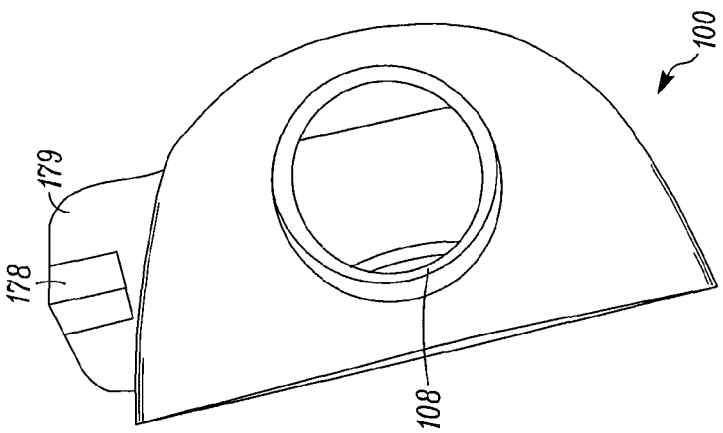

An illustration of the visual feedback provided by the orientation indicator 158 is shown in FIGS. 8A-C. As seen in FIGS. 8A and 8C, when the OPEP device 100 is rotated about the axis perpendicular to the cylindrical support surfaces 166 described above to an orientation not suitable for or ideal to the administration of OPEP therapy, the orientation indicator 158 moves away from the center of the capsule 178 and behind the non-transparent material 179 surrounding the capsule 178. In contrast, while the OPEP device 100 is maintained in an orientation suitable and/or ideal for the administration of OPEP therapy, the indicator 158 remains in the center portion of the capsule 178, as shown in FIG. 8B. In this way, the orientation indicator 158 provides the user with visual feedback of orientations of the OPEP device 100 suitable and/or ideal for the administration of OPEP therapy and permits him or her to change the orientation of the OPEP device 100 in response thereto.

Figure 9A:
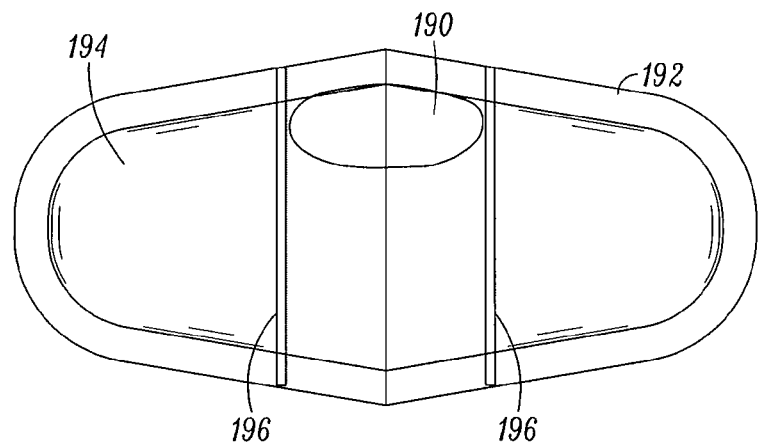
Figure 9B:
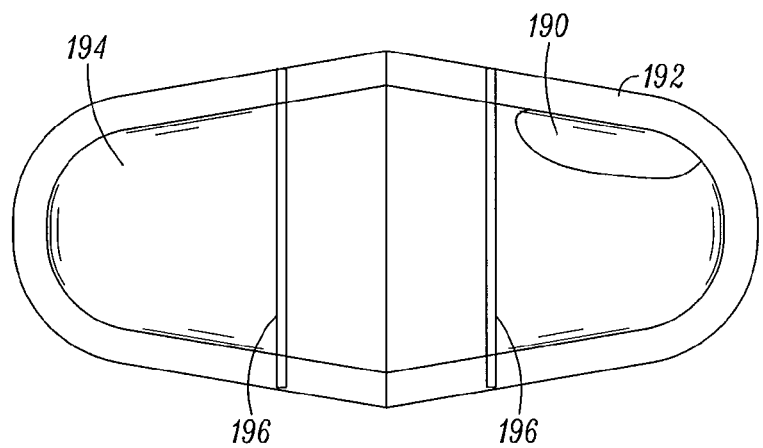

Alternatively, as shown in FIGS. 9A-9B, an orientation indicator 190 may comprise a fluid, such as a gas or low-density liquid, which is enclosed by a capsule 192 filled with a higher-density fluid 194. Thus, the orientation indicator 190 may appear to the user as a bubble or mass enclosed within the capsule 192. As with the previously described example, and depending on the geometry of the capsule 192, the orientation indicator 190 may float to portions of the capsule 192 in response to a change in orientation of the capsule 192 and associated device. Likewise, an indicia 196 may be provided on the capsule 192 identifying the portion of the capsule in which the presence of the orientation indicator 190 indicates an orientation of the associated device suitable and/or ideal for operation, for example, the administration of OPEP therapy.

Figure 10:
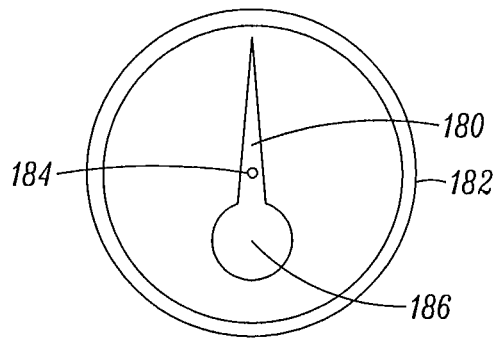
Figure 11A:
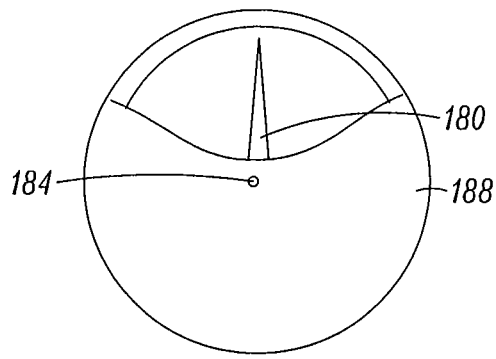
Figure 11B:
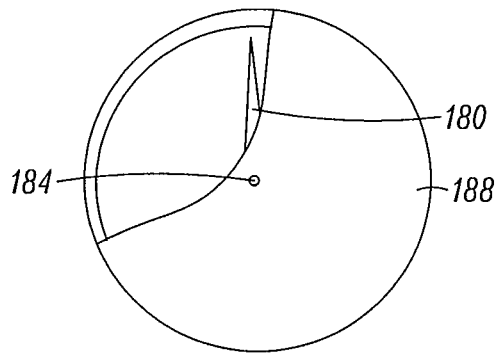

Turning to FIGS. 10-11B, an alternative embodiment of an orientation indicator 180 is shown. In FIG. 10, the orientation indicator 180 takes the form of a meter needle pivotably attached to a housing 182 about a pin 184. As with the previously described embodiment, the housing 182 may be positioned on an OPEP device or other respiratory device in a location such that the user may view the orientation indicator during operation of the device. The orientation indicator 180 further comprises a counterweight 186 disposed at one end of the meter needle such that, as the orientation of the associated device is changed, the orientation indicator rotates about pin 184 under the force of gravity to maintain alignment with the direction of gravity.

As shown in FIGS. 11A and 11B, a cover 188 removably attached to the housing 182 encloses the orientation indicator 180 and provides the user with an indicia of the range of orientations of the associated device suitable and/or ideal for its operation. For example, as shown in FIGS. 11A and 11B, respectively representing upright and rotated positions of the associated device, so long as the appropriate end of the orientation indicator is visible to a user (i.e., not the counterweight 186), the device is in an orientation suitable and/or ideal for the administration of OPEP therapy. Alternative predetermined ranges of orientations may be selected by changing the shape of the cover to show or hide a larger portion of the housing 182.

Figure 12A:
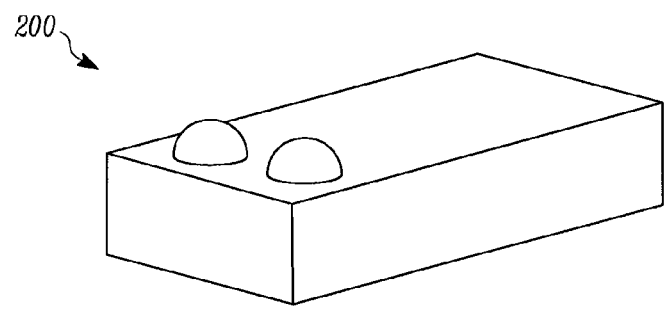
Figure 12B:
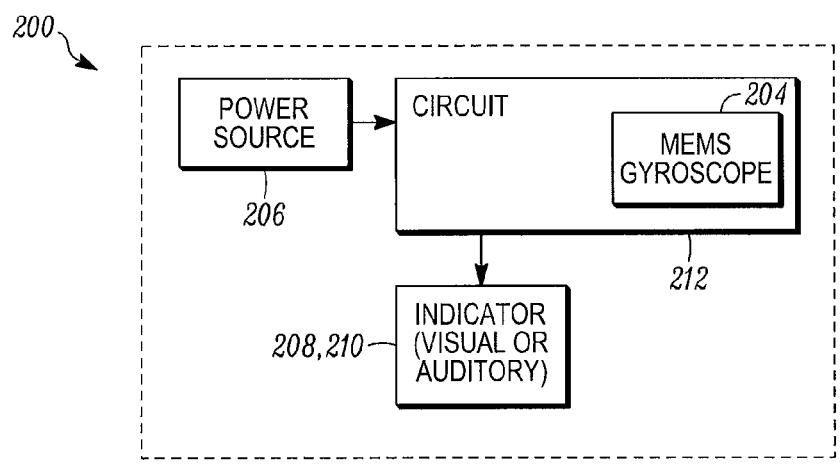
Figure 12C:
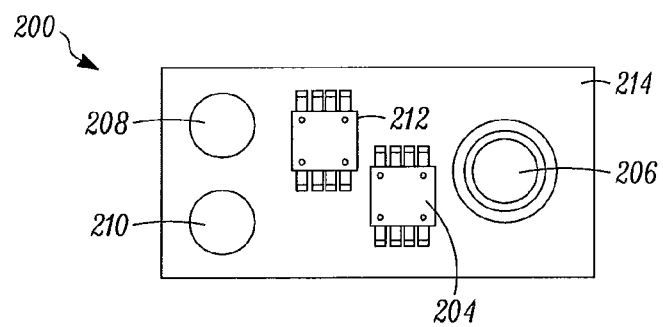

Referring now to FIGS. 12A-C, representative views of an alternative embodiment of an orientation indicator 200 are shown. FIG. 12A is a perspective view of the orientation indicator 200 contained within housing 202; FIG. 12B is a block diagram showing the operating components of the orientation indicator 200; and, FIG. 12C is a top view of the orientation indicator 200 without the housing 202.

In general, the operating components of the orientation indicator 200 comprise a micro electro-mechanical gyroscope 204, a power source 206, one or more visual or auditory indicators 208, 210, and a circuit 212 for connecting all of the same and analyzing the output of the gyroscope 204. These operating components are mounted on a circuit board 214.

Those skilled in the art will appreciate that the micro electro-mechanical gyroscope 204 may be selected from any number of commercially available products, and the power source 206 may be selected from any number of commercially available batteries. Likewise, the one or more visual indicators may be selected from any number of lighting products, such as, for example, one or more different colored light emitting diodes. Similarly, the one or more auditory indicators may by selected from any number of audio signaling devices, including buzzers, beepers, bells, alarms, speakers, or the like.

In operation, the orientation indicator 200 may be connected to the housing 102 of the OPEP device 100 and configured in any number of ways for indicating an orientation of the housing 102 of the OPEP device 100 predetermined to be suitable and/or ideal for administration of OPEP therapy to a user. For example, the one or more visual indicators may include a green light configured to illuminate when the housing 102 of the OPEP device 100 is in a position predetermined to be suitable for administration of OPEP therapy. Or, the one or more visual indicators may also include a red light configured to illuminate when the housing 102 of the OPEP device 100 is in a position predetermined to be less suitable for the administration of OPEP therapy. Alternatively, the illumination of a single light may indicate a suitable or less suitable position of the housing 102. Similarly, the orientation indicator 200 may provide one or more auditory indicators, such as a beep or a warning tone, indicative of a suitable or a less suitable position of the housing 102. Likewise, any combination or variation of the above examples may be used to indicate the suitability of a particular orientation of the housing.

As previously explained, the suitable and/or ideal operation of the OPEP device 100 may be maintained when the OPEP device 100 is rotated about the axis defined between the cylindrical support surfaces 166. However, when the OPEP device 100 is rotated perpendicular to the axis defined between the cylindrical support surfaces 166, the desired and/or ideal operating conditions are impacted, such that visual or auditory feedback from an orientation indicator becomes relevant. Likewise, for any respiratory device that may benefit from the device's orientation for suitable and/or ideal operation, it is envisioned that the orientation indicators described above would provide users with visual or auditory feedback indicative of suitable and/or ideal orientations for a device's operation. Examples of other respiratory devices on which the orientation indicators described above may be mounted include nebulizers, pressurized metered dose inhalers, aerosol holding chambers, peak flow meters and so on.

Figure 13:
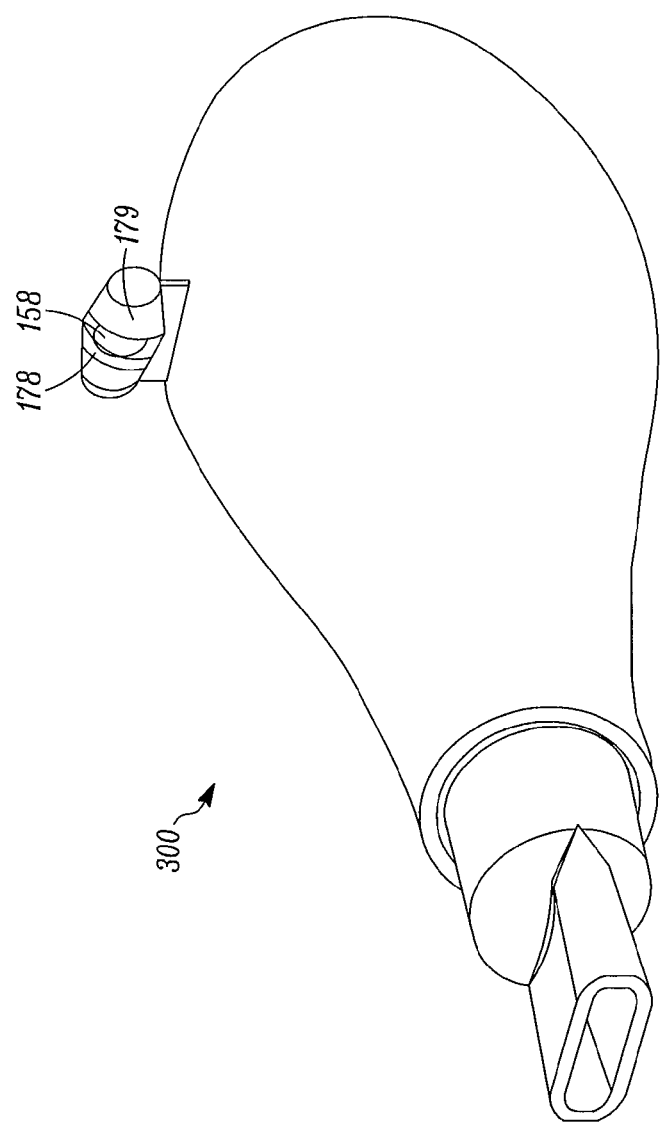
Figure 14:
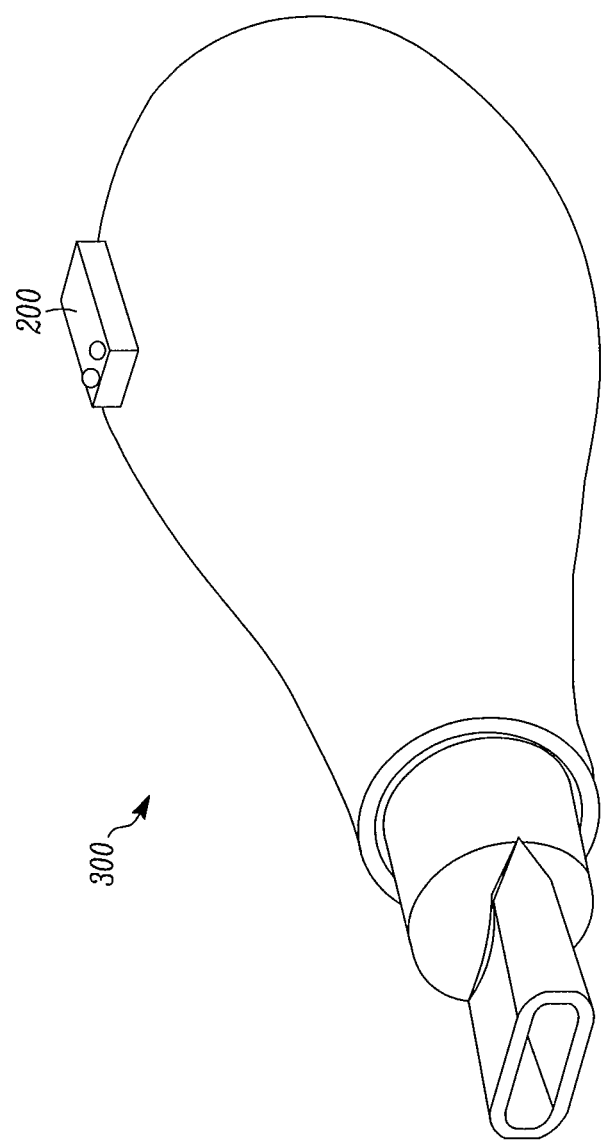
Figure 15:
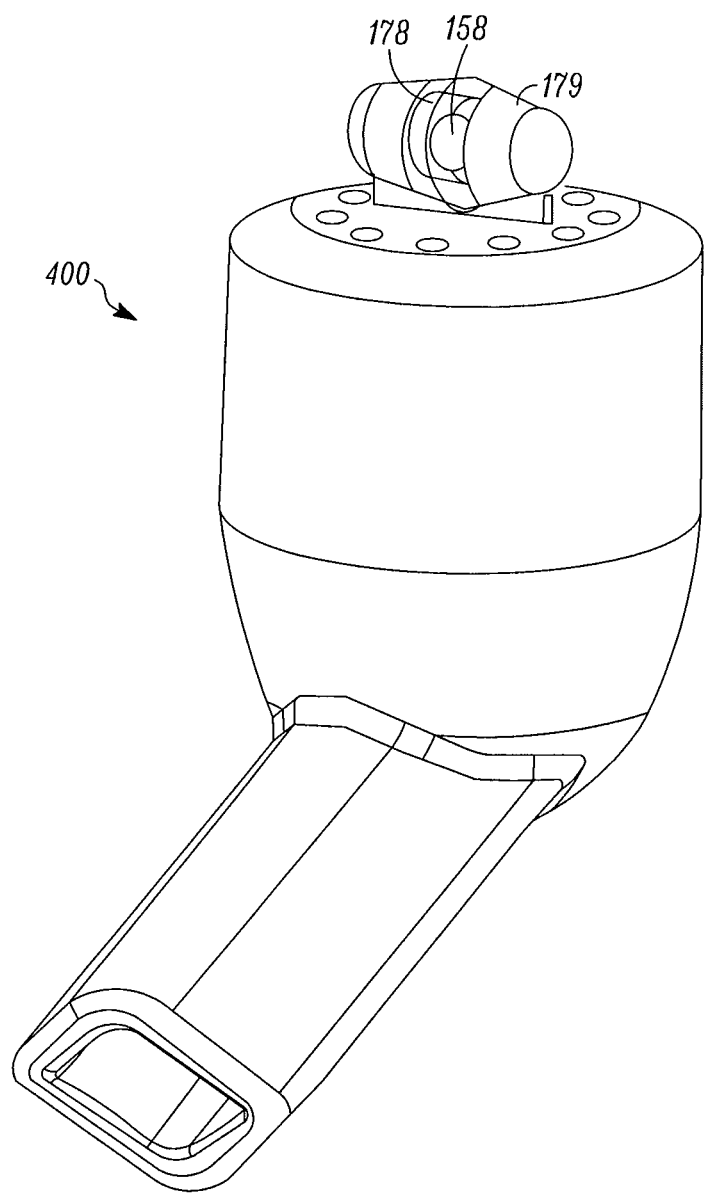
Figure 16:
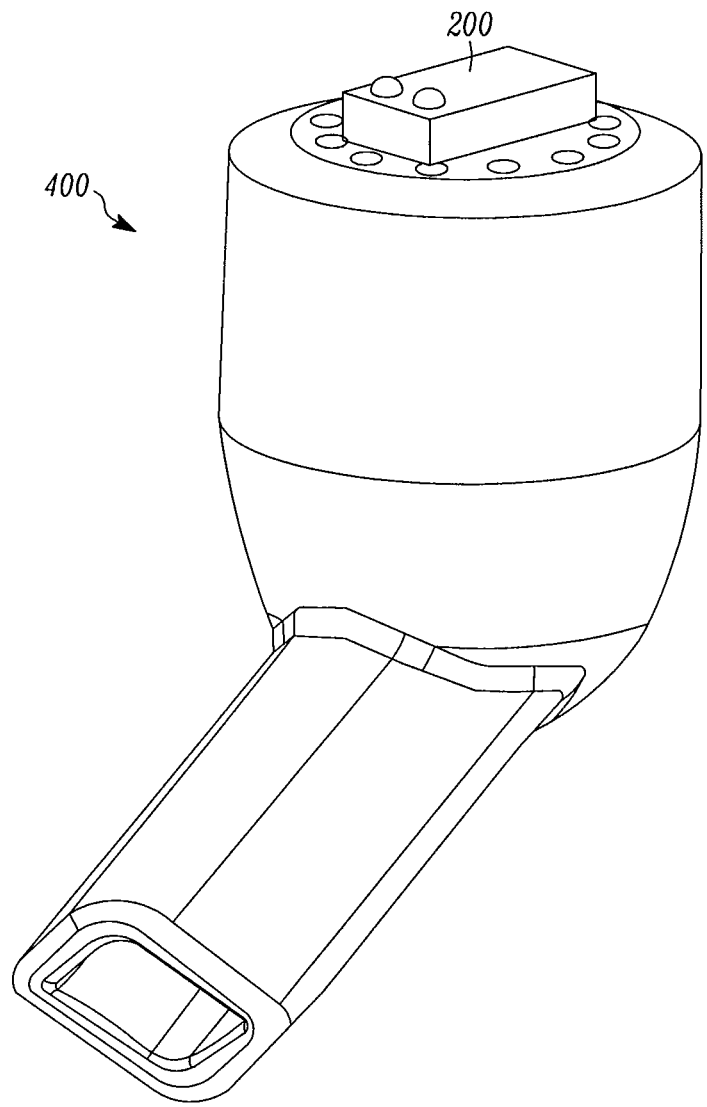

For example, the orientation indicators described above may be utilized on other commercially available OPEP devices. FIGS. 13-14 show the disclosed orientation indicators mounted on an embodiment of an OPEP device 300 shown and described in U.S. Pat. Nos. 6,776,159 and 7,059,324, the entireties of which are herein incorporated by reference, and commercially available under the trade name ACAPELLA® from Smiths Medical of St. Paul, Minn. Likewise, FIGS. 15-16 show the disclosed orientation indicators mounted on an embodiment of an OPEP device 400 shown and described in U.S. Pat. No. 5,018,517, the entirety of which is herein incorporated by reference, and commercially available under the trade name FLUTTER® from Axcan Scandipharm Inc. of Birmingham, Ala.

Figure 17:
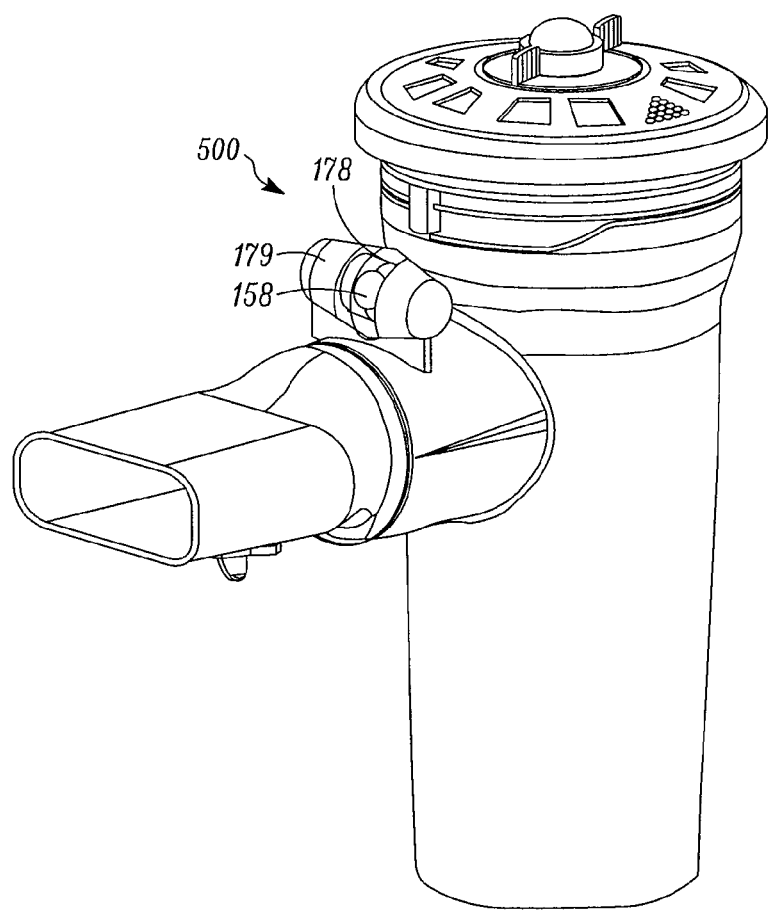
Figure 18:
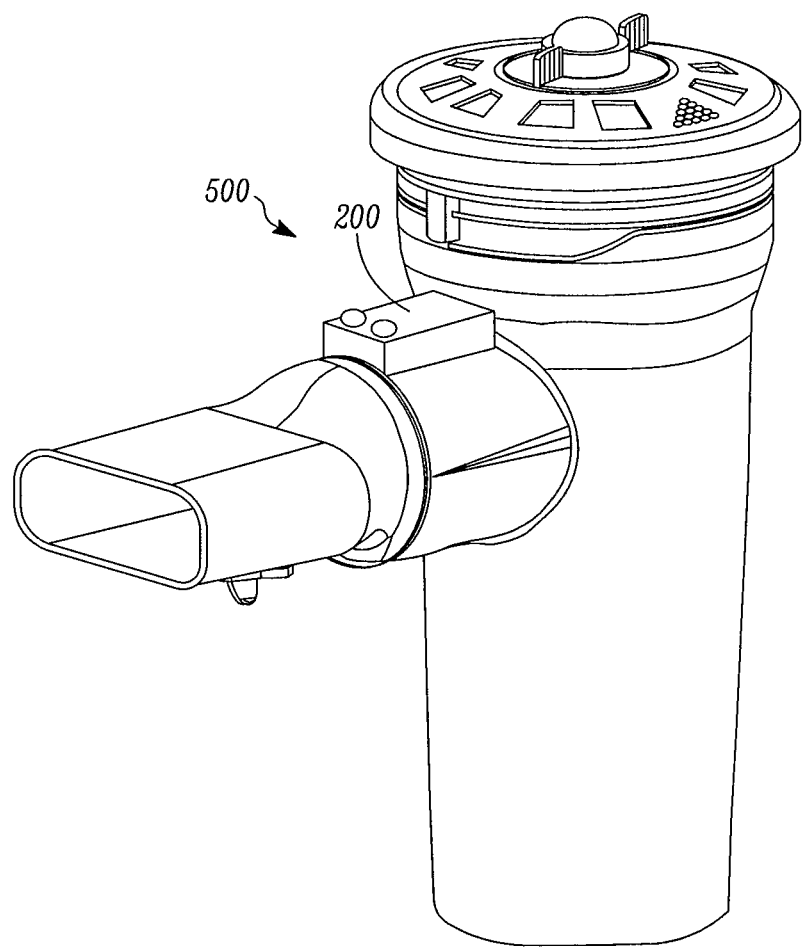

In another example, the orientation indicators described above may be utilized on commercially available nebulizers. FIGS. 17-18 show the disclosed orientation indicators mounted on an embodiment of a nebulizer 500 shown and described in U.S. Pat. Nos. 7,568,480 and 7,905,228, the entireties of which are herein incorporated by reference, and commercially available under the trade name AERO-ECLIPSE® II from Trudell Medical International of London, Canada. In general, nebulizers include a reservoir of a liquid medicament and a source of pressurized gas for aerosolizing the liquid. Typically, the reservoir is in fluid communication with the pressurized gas, for example, by means of a channel through which the liquid medicament may be drawn from the reservoir. However, in such embodiments, the orientation of the reservoir may be critical in preventing the liquid medicament from leaking out of the reservoir, and in permitting the liquid medicament to be entrained up the channel. In that regard, the typical nebulizer may benefit from the visual or auditory feedback of the orientation indicators described above.

The foregoing description has been presented for purposes of illustration and description, and is not intended to be exhaustive or to limit the inventions to the precise forms disclosed. It will be apparent to those skilled in the art that the present inventions are susceptible of many variations and modifications coming within the scope of the following claims. For example, multiple orientation indicators may be utilized on devices whose suitable and/or ideal operation is impacted by movement of the device about more than one axis of rotation. Alternatively, the geometry of a capsule enclosing an orientation indicator on such a device may be configured such that the orientation indicator is capable of moving in more than one direction, thereby providing a more dynamic indication of the suitability of the orientation of the device.

What is claimed is:

1. A respiratory device comprising:
a housing enclosing a chamber; and
an orientation indicator moveable with respect to the housing between a first position indicative of an orientation of the housing predetermined to be suitable for operation of the respiratory device, and a second position indicative of an orientation of the housing predetermined to be less suitable for operation of the respiratory device, wherein the orientation indicator is positioned in a location on the respiratory device visible to a user during the operation of the respiratory device; and
wherein the orientation indicator is a fluid.

2. The respiratory device of claim 1, wherein the orientation indicator moves in response to a change in the orientation of the housing.

3. The respiratory device of claim 1, wherein a weight of the orientation indicator biases the orientation indicator in the direction of gravity.

4. The respiratory device of claim 1, wherein the orientation indicator is moveable in at least one direction.

5. The respiratory device of claim 1 further comprising a capsule enclosing the orientation indicator, the capsule comprising an indicia for identifying a portion of the capsule in which the presence of the orientation indicator indicates an orientation of the housing predetermined to be suitable for operation of the respiratory device.

6. The respiratory device of claim 5, wherein the capsule is shaped so that the orientation indicator moves to the first position in response to a change in the orientation of the housing to an orientation predetermined to be suitable for operation of the respiratory device.

7. The respiratory device of claim 1, wherein the respiratory device is an oscillating positive expiratory pressure device.

8. The respiratory device of claim 1, wherein the respiratory device is a nebulizer.

9. A respiratory device comprising:
a housing enclosing a chamber; and,
an orientation indicator configured to provide visual or auditory feedback to a user indicative of a suitability of an orientation of the housing predetermined to be suitable for administration of a respiratory therapy; and,
wherein the orientation indicator comprises a micro electro-mechanical system gyroscope configured to sense the orientation of the housing.

10. The respiratory device of claim 7, further comprising:
a chamber inlet;
a chamber outlet;
a channel positioned in an exhalation flow path between the chamber inlet and the chamber outlet; and,
an air flow regulator moveable with respect to the channel.

11. A respiratory device comprising:
a housing enclosing a chamber; and,
an orientation indicator moveable with respect to the housing between a first position indicative of an orientation of the housing predetermined to be suitable for operation of the respiratory device, and a second position indicative of an orientation of the housing predetermined to be less suitable for operation of the respiratory device, wherein the orientation indicator is positioned in a location on the respiratory device visible to a user during the operation of the respiratory device; and,
wherein the orientation indicator is a sphere.

12. The respiratory device of claim 11, wherein the orientation indicator moves in response to a change in the orientation of the housing.

13. The respiratory device of claim 11, wherein a weight of the orientation indicator biases the orientation indicator in the direction of gravity.

14. The respiratory device of claim 11, wherein the orientation indicator is moveable in at least one direction.

15. The respiratory device of claim 11, further comprising a capsule enclosing the orientation indicator, the capsule comprising an indicia for identifying a portion of the capsule in which the presence of the orientation indicator indicates an orientation of the housing predetermined to be suitable for operation of the respiratory device.

16. The respiratory device of claim 11, wherein the capsule is shaped so that the orientation indicator moves to the first position in response to a change in the orientation of the housing to an orientation predetermined to be suitable for operation of the respiratory device.

17. The respiratory device of claim 11, wherein the respiratory device is an oscillating positive expiratory pressure device.

18. The respiratory device of claim 11, wherein the respiratory device is a nebulizer.

19. The respiratory device of claim 17, further comprising:
a chamber inlet;
a chamber outlet;
a channel positioned in an exhalation flow path between the chamber inlet and the chamber outlet; and,
an air flow regulator moveable with respect to the channel.

20. A respiratory device comprising:
a housing enclosing a chamber; and,
an orientation indicator moveable with respect to the housing between a first position indicative of an orientation of the housing predetermined to be suitable for operation of the respiratory device, and a second position indicative of an orientation of the housing predetermined to be less suitable for operation of the respiratory device, wherein the orientation indicator is positioned in a location on the respiratory device visible to a user during the operation of the respiratory device; and,
wherein the orientation indicator is a meter needle.

21. The respiratory device of claim 20, wherein the orientation indicator moves in response to a change in the orientation of the housing.

22. The respiratory device of claim 21, wherein a weight of the orientation indicator biases the orientation indicator in the direction of gravity.

23. The respiratory device of claim 21, wherein the orientation indicator is moveable in at least one direction.

24. The respiratory device of claim 21, further comprising a capsule enclosing the orientation indicator, the capsule comprising an indicia for identifying a portion of the capsule in which the presence of the orientation indicator indicates an orientation of the housing predetermined to be suitable for operation of the respiratory device.

25. The respiratory device of claim 20, wherein the capsule is shaped so that the orientation indicator moves to the first position in response to a change in the orientation of the housing to an orientation predetermined to be suitable for operation of the respiratory device.

26. The respiratory device of claim 20, wherein the respiratory device is an oscillating positive expiratory pressure device.

27. The respiratory device of claim 20, wherein the respiratory device is a nebulizer.

28. The respiratory device of claim 26, further comprising:
a chamber inlet;
a chamber outlet;
a channel positioned in an exhalation flow path between the chamber inlet and the chamber outlet; and,
an air flow regulator moveable with respect to the channel.

29. A respiratory device comprising:
a housing enclosing a chamber; and,
an orientation indicator configured to provide visual or auditory feedback to a user indicative of a suitability of an orientation of the housing predetermined to be suitable for administration of a respiratory therapy;
wherein the orientation indicator comprises at least one light for indicating the suitability of the orientation of the housing for the administration of the respiratory therapy.

30. A respiratory device comprising:
a housing enclosing a chamber; and,
an orientation indicator configured to provide visual or auditory feedback to a user indicative of a suitability of an orientation of the housing predetermined to be suitable for administration of a respiratory therapy;
wherein the orientation indicator comprises an audio signaling device for indicating the suitability of the orientation of the housing for the administration of the respiratory therapy.

* * * * *